(12) United States Patent
Zhang (10) Patent No.: US 11,022,558 B2
(45) Date of Patent: Jun. 1, 2021

(54) COAGULATION ANALYZER AND COAGULATION ANALYSIS METHOD

(71) Applicant: SHENZHEN THISTORY BIO-MEDICAL CO.,LTD, Shenzhen (CN)

(72) Inventor: Lihua Zhang, Shenzhen (CN)

(73) Assignee: SHENZHEN THISTORY BIO-MEDICAL CO., LTD, Shenzhen (CN)

(*) Notice: Subject to any disclaimer, the term of this patent is extended or adjusted under 35 U.S.C. 154(b) by 211 days.

(21) Appl. No.: 15/992,212

(22) Filed: May 30, 2018

(65) Prior Publication Data

US 2019/0033221 A1    Jan. 31, 2019

(30) Foreign Application Priority Data

Jul. 27, 2017   (CN) .......................... 201710627022.4

(51) Int. Cl.
| | | |
|---|---|---|
| *G01N 33/86* | (2006.01) | |
| *G01N 21/82* | (2006.01) | |
| *G01N 33/50* | (2006.01) | |
| *G01N 33/49* | (2006.01) | |

(52) U.S. Cl.
CPC ............ *G01N 21/82* (2013.01); *G01N 33/86* (2013.01); *G01N 33/4905* (2013.01)

(58) Field of Classification Search
CPC ........ G01N 33/86; G01N 33/50; G01N 33/48; G01N 21/82; G01N 21/77; G01N 21/75

USPC .............................................. 436/69; 422/50
See application file for complete search history.

(56) References Cited

U.S. PATENT DOCUMENTS

2008/0044912 A1* 2/2008 Yamamoto ......... G01N 33/4905
436/69
2015/0044780 A1* 2/2015 Kurz ................ G01N 33/54393
436/501

FOREIGN PATENT DOCUMENTS

CN   201720925726.5   *  7/2017 ............. G01N 33/86

* cited by examiner

*Primary Examiner* — Christine T Mui
(74) *Attorney, Agent, or Firm* — Bayramoglu Law Offices LLC (57) ABSTRACT

The present invention discloses a coagulation analyzer and a coagulation analysis method which relate to the technical field of medical instruments. The coagulation analyzer includes an optical coagulation analysis module, a sample interference analysis module, a magnetic coagulation analysis module, and a test transfer module. The coagulation analyzer uses the sample interference analysis module to determine whether an interferent in the sample has effect on the coagulation test result of the optical coagulation analysis module. If the interferent in the sample has no effect on the coagulation test result, the optical coagulation analysis module is used to perform the coagulation analysis and report the test result. If the interferent in the sample has effect on the coagulation test result, the test transfer module is used to transfer the test to the magnetic coagulation analysis module to perform the coagulation analysis and report the test result.

12 Claims, 6 Drawing Sheets

COAGULATION ANALYZER AND COAGULATION ANALYSIS METHOD

CROSS REFERENCE TO RELATED APPLICATIONS

This application is based upon and claims priority to Chinese Patent Application No. 201710627022.4, filed on Jul. 27, 2017 the entire contents of which are incorporated herein by reference.

TECHNICAL FIELD

The present invention relates to the technical field of medical instruments, and particularly to a coagulation analyzer and a coagulation analysis method.

BACKGROUND

With the development of medical instruments and biotechnology, and the progress made in the basic theory of hemostasis and thrombosis and the application thereof, automatic coagulation analyzers have been developed rapidly and widely used in the diagnosis and treatment process.

The leading international coagulation device manufacturers such as Sysmex, Werfen, and Stago dominate the mainstream market. Chinese manufacturers such as Succeeder, Precil, Rayto and so on also launched coagulation analyzer products. Generally, there are three approaches to the testing of blood coagulation, namely, coagulation, immunonephelometry, and colorimetry. Based on the reaction principle of the immunoturbidimetry and colorimetry, optical method is usually used by the manufacturers for the testing. For the coagulation approach, two methods are mainly used by the leading manufacturers, i.e. magnetic bead (which refers to magnetically drivable particle in the context of the present invention) method and optical method. These two methods have their own advantages and disadvantages. Currently, the optical method is dominant in the market. However, during the test of coagulation items, when interferents of hemolysis, jaundice, and lipemia etc. occur in the sample, the measurement result of the optical method will be affected. The magnetic bead method uses magnetic force to drive a demagnetized steel bead (magnetically drivable particle) to move in the sample. When the sample clots, the movement of the demagnetized steel bead stops, gradually. A steel bead particle displacement sensing device (usually a magnetic displacement sensing) is used to sense the movement of the demagnetized steel bead and calculate the clot time. By doing so, the optical interference of hemolysis, jaundice, and lipemia to the coagulation test can be avoided.

For the magnetic bead based instruments, the items of coagulation approach are tested by the magnetic bead method, the items of immunoturbidimetry and the colorimetry approaches are tested by the optical method. For optical method based instruments, the items of the coagulation, immunoturbidimetry, and colorimetry approaches are tested by the optical method.

Because the magnetic bead based instrument should be equipped with magnetic bead method test channel and optical method test channel at the same time, the instrument is more complex and the challenges for reliability are more. Each testing analysis cup is provided with a magnetic bead, resulting in an increased cost of consumables for an individual test. For the items tested by immunoturbidimetry approach (for example, D-DIMER, FDP, etc.) and the items tested by colorimetry approach (for example, anti-thrombin III, etc.), the disadvantages of using the analysis cup with magnetic bead of the magnetic bead based instrument are more obvious. Increased amount of reagents are required, so the cost for customers is further increased. Moreover, the magnetic bead affects the mixing effect, and thus reduces the accuracy of measurement.

SUMMARY

The coagulation analyzer and the coagulation analysis method provided by the present invention use a sample interference analysis module to determine whether an interferent in the sample has effect on the test results of the coagulation items in the optical coagulation analysis channel. If the interferent in the sample has no effect on the test results, the optical coagulation analysis module is used to perform the measurement and report the test result. If the interferent in the sample has effect on the test results, a test transfer module is used to transfer the test to a magnetic coagulation analysis module to perform the measurement and report the test result.

For the coagulation test samples in the hospital, merely a few samples are interfered samples, and most of the samples are the normal samples, so the method of the present invention effectively reduces the frequency of use of the magnetic coagulation analysis module. For example, in a hospital where about 40 samples are tested in a day, the magnetic coagulation analysis module is merely used about once or twice, thus compared with the magnetic bead based instrument, the cost is reduced while the situation where an accurate result cannot be reported by the optical method based instrument as a result of the occurrence of lipemia, jaundice, and hemolysis in the samples and thus affecting the follow-up treatment can be avoided. Moreover, most of the tests of the present invention are accomplished by the optical method, so the characteristics of low cost, high accuracy, and high reliability of the optical method based instruments are kept.

In the magnetic bead instruments, when the items of immunoturbidimetry (for example, d-dimer, FDP, etc.), and the items of colorimetry (for example, anti-thrombin III, etc.) are tested, the optical method test channel is used to perform the measurement and the analysis cup with magnetic bead is still used, namely, the analysis cup with magnetic bead is used even if the magnetic bead test channel is not used. The analysis cup is designed with a space reserved for the movement of the magnetic bead, so the magnetic bead occupies the space in the analysis cup, thereby limiting the design for operations such as adding sample, mixing etc. For example, the design for adding sample needs to consider the collision between the sample adding probe and the magnetic bead, and the design of mixing also needs to consider the effects of the magnetic bead. Moreover, when the cup with magnetic bead is used for optical measurement, the optical path needs to avoid the magnetic bead, so that the amount of reagent used and the design of optical path are both affected.

The optical coagulation analysis module of the coagulation analyzer of the present invention uses an analysis cup without particle, thereby reducing the cost of analysis cup and reagent, while the design in aspects of mixing, and loading of the analysis cup is easier and more reliable. The magnetic coagulation analysis module uses an analysis cup with particle, so the advantage of anti-sample-interference of magnetic bead method in the test of the coagulation items is maintained. The interfered sample can be transferred to the magnetic analysis module to be tested. In the hospital where about 40 samples are tested in a day, the magnetic module is merely used once or twice, so most of the samples are tested in the optical coagulation analysis module, and the analysis cup used is the analysis cup without particle, thereby greatly improving the economic efficiency of the test while keeping the advantage of anti-interference of the magnetic bead method.

In order to overcome the drawbacks and deficiencies of the above-mentioned prior art, based on the above-mentioned design principles, the present invention provides a coagulation analyzer including:

an optical coagulation analysis module which uses an analysis cup without particle for an optical coagulation analysis;

a sample interference analysis module for analyzing an effect of a sample interference on the optical coagulation analysis, and determining a coagulation test affected by the sample interference;

a magnetic coagulation analysis module which uses an analysis cup with a magnetically drivable particle for a magnetic coagulation analysis; and a test transfer module for transferring the coagulation test affected by the sample interference to the magnetic coagulation analysis module.

The coagulation analyzer uses the sample interference analysis module to determine whether the interferent in the sample has effect on the coagulation test result of the optical coagulation analysis module. If the interferent in the sample has no effect on the coagulation test result, the optical coagulation analysis module is used to perform the coagulation analysis and report the test result. If the interferent in the sample has effect on the coagulation test result, the test transfer module is used to transfer the test to the magnetic coagulation analysis module to perform the coagulation analysis and report the coagulation test result.

Since the optical coagulation analysis module uses an analysis cup without particle, the cost of the analysis cup and the reagent is reduced, and the design in aspects of mixing, and loading of the analysis cup is easier and more reliable. Since the magnetic coagulation analysis module uses the analysis cup with particle, the advantage of the anti-sample-interference of the magnetic bead method in the test of the coagulation items is maintained. The interfered sample can be transferred to the magnetic analysis module to be tested. In the hospital where about 40 samples are tested in a day, the magnetic module is used about once or twice, so most of the samples are tested in the optical coagulation analysis module, and the analysis cup used is the analysis cup without particle, thereby greatly improving the economic efficiency of the test, while keeping the advantage of anti-interference of the magnetic bead method.

In a preferred implementation, the sample interference analysis module using an optical analysis method includes a first light source component, a first light reception component, and a sample interference data processing unit. The first light reception component collects optical signals of a transmitted light or a scattered light of a sample or a mixture of the sample and a reagent irradiated by the first light source component. The sample interference data processing unit determines whether the interferent in the sample has effect on a part of or a whole coagulation test of the optical coagulation analysis module.

In a preferred implementation, the optical coagulation analysis module includes a second light source component and a second light reception component. The second light reception component collects optical signals of the transmitted light or the scattered light of the sample or the mixture of the sample and the reagent irradiated by the second light source component to complete the optical coagulation test of the sample.

Preferably, a light source of the first light source component and the second light source component is a light source device such as a halogen lamp, a semiconductor laser, or an LED light source etc.

In a preferred implementation, the first light source component and the second light source component are the same component.

In a preferred implementation, the first light reception component and the second light reception component are the same component.

In a preferred implementation, the magnetic coagulation analysis module includes a magnetic drive component and a particle displacement sensing component. The magnetic drive component drives the magnetically drivable particle to displace. The particle displacement sensing component detects a movement of the magnetically drivable particle and complete the coagulation test of the sample. The magnetic drive module drives the magnetically drivable particle to move regularly. The particle displacement sensing component detects the movement of the particle. When the clot occurs, a change of the movement of the particle is detected to complete the coagulation test of the sample. The particle displacement sensing component may use an optical displacement sensing, a magnetic displacement sensing, or other detection means that can capture the change of the movement of the particle driven by magnetic force. Preferably, magnetic displacement sensing is used.

In a preferred implementation, the magnetically drivable particle may be pre-loaded into the analysis cup to be provided to the coagulation analyzer, or be automatically loaded into the analysis cup by the coagulation analyzer. Preferably, the magnetically drivable particle is demagnetized steel bead.

In a preferred implementation, the coagulation analyzer further includes a reagent placing module for placing coagulation analysis reagents. For example, the reagent of coagulation test such as prothrombin time (PT), activated partial thromboplastin time (APTT), fibrinogen (FIB), thrombin time (TT), anti-thrombin III (AT-III), FDP, D-DIMER, Protein C, Protein C, cleaning solution, coagulation factor etc. When the reagent needs to be kept stable in the instrument, the reagent placing module may further include a cooling component for maintaining a low temperature storage condition for the reagent. Preferably, the low temperature is ranged from 10° C.-15° C.

In a preferred implementation, the test transfer module includes a liquid transfer module including one or more liquid transfer components. The liquid transfer component completes the operation of transferring the coagulation test to the magnetic coagulation analysis module by a liquid transfer operation of the sample and/or reagent and/or the mixture of the sample and the reagent.

In a preferred implementation, the test transfer module includes an analysis cup transfer module including one or more analysis cup transfer components. The analysis cup transfer component completes the operation of transferring the coagulation test to the magnetic coagulation analysis module by a transfer operation of the analysis cup.

In a preferred implementation, the test transfer module may also transfer the interference sample to a position where the magnetic coagulation analysis module is enabled to perform the measurement. The magnetic coagulation analysis module may be separately equipped with a liquid transfer device to suck the interference sample and then transfer to the analysis cup with magnetic bead.

In a preferred implementation, the analysis cup without particle and the analysis cup with the magnetically drivable particle have different geometrical structural characteristics.

Figure 1:
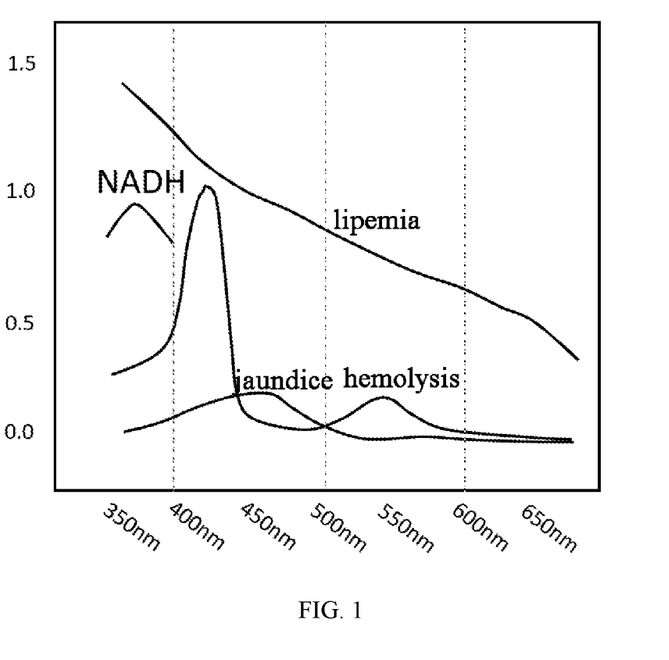
FIG. 1 is an absorption spectrum diagram of interferences of lipemia, jaundice and hemolysis.

Generally, plasma samples are used in the coagulation tests, sometimes with the occurrence of interferents of hemolysis, jaundice, lipemia etc. As shown in FIG. 1, samples with lipemia, jaundice and hemolysis will generate optical absorption signals, and the absorption is distributed in the wavelength range of 300-800 nm of the absorption signals. Especially for lipemia, the distribution width of the absorption signals is wider. When hemolysis occurs, there is heme in the samples, and when jaundice occurs, there is bilirubin in the samples. These two substances have stronger light absorption in a range of about 400-600 nm, which would interfere with the background of the signals, and the absorption peak will have a long tail. It is difficult to overcome this interference when the optical method is used in the test, especially for the coagulation tests with higher sensitivity requirements, the interference is even more obvious. For samples with lipemia, there are lipid particles in the blood that would reflect and scatter the incident light, thereby affecting the detection of the optical signals, and reducing the sensitivity of sample analysis. The use of some drugs will also affect the measurement of the optical signals in the blood.

An optical interference recognition is performed on the coagulation sample or the mixture of sample and reagent (which are collectively referred as the to-be-recognized sample). Preferably, the to-be-recognized sample is irradiated by lights with a plurality of wavelengths ranged from 300 nm-800 nm in the recognition to detect a transmitted light intensity or a scattered light intensity of the to-be-recognized sample (preferably, transmitted light intensity). The presence of interferents, which can affect the coagulation test in the to-be-recognized sample, is determined by the optical interference recognition.

Preferably, the specific optical interference recognition method includes selecting a sample having no effect on the coagulation test result (including a sample without optical interference and a sample with a low content of the optical interferent which is insufficient to affect the coagulation test result); measuring a transmitted light intensity or scattered light intensity in a normal condition without interference; calculating characteristic values such as transmittivity, absorbance value, or scattered light intensity value; counting a distribution of eigenvalues and setting a threshold. After the to-be-recognized sample is irradiated by the light source, the light reception component acquires an intensity signal of the transmitted light or the scattered light and calculates the eigenvalues such as transmittivity, absorbance value, or the scattered light intensity value. If the eigenvalue exceeds the pre-set threshold, it is determined that the sample interference has an effect on the coagulation test.

The optical interference recognition is completed by the sample interference analysis module. The sample interference analysis module and the optical coagulation analysis module may be a common module, i.e., sharing all module components, different modules that share a part of components (e.g., light source component), or independent modules that do not share any component. Specifically, the optical interference recognition of the to-be-recognized sample may be realized in the optical coagulation measurement position of the optical coagulation analysis module by using the analysis cup without particle. Specifically, the optical interference recognition may be performed in the specific optical interference recognition position by using the sample in the original sample tube, directly. Specifically, the optical interference recognition of the sample or the mixture of sample and reagent (collectively referred as the to-be-recognized sample) in the analysis cup may be performed in the specific optical interference recognition position.

The coagulation test unaffected by sample interference is performed in the optical coagulation analysis channel and the test results are reported. If the coagulation test is determined to be affected by the sample interference, the test is transferred to the magnetic coagulation analysis channel by the test transfer device to perform the measurement and report the test results. The magnetic coagulation analysis module uses the magnetic force to drive the movement of a macroscopic steel bead particle. The particle movement itself is unaffected by the interferents. The movement of the driven macroscopic steel bead particle may be sensed by the particle displacement sensing component, and the magnetic displacement sensing is generally preferred, so the magnetic coagulation analysis module is also unaffected by the optical interferents in the sample.

A coagulation analysis method provided by the present invention specifically includes the following steps:

(1) performing an optical interference recognition for a sample or a mixture of the sample and a reagent in a sample interference analysis module;

(2) determining whether an interferent in the sample has an effect on a test result of coagulation items of an optical coagulation analysis channel;

(3) using the optical coagulation analysis channel of an optical coagulation analysis module to perform a measurement and report the test result if the interferent in the sample has no effect on the test result.

(4) using a test transfer module to transfer the test to a magnetic coagulation analysis channel of a magnetic coagulation analysis module to perform the measurement and report the test result if the interferent in the sample has effect on the test result.

In a preferred implementation, the optical coagulation analysis channel uses an analysis cup without particle.

In a preferred implementation, the magnetic coagulation analysis channel uses an analysis cup with magnetically drivable particle.

In a preferred implementation, the magnetically drivable particle may be pre-loaded into the analysis cup to be provided to the magnetic coagulation analysis module, or automatically loaded into the analysis cup by the coagulation analyzer. The magnetically drivable particle is a demagnetized steel bead.

In a preferred implementation, the optical interference recognition includes determining whether the optical interference has effect on the coagulation test by detecting the optical signals of transmitted light or the scattered light after the sample or the mixture of sample and reagent is irradiated by a light source optical signal.

In a preferred implementation, the test transfer module includes a liquid transfer module including one or more liquid transfer components. The liquid transfer component completes the operation of transferring the coagulation test to the magnetic coagulation analysis channel of the magnetic coagulation analysis module by a liquid transfer operation of the sample and/or the reagent and/or the mixture of the sample and the reagent.

In a preferred implementation, the test transfer module includes an analysis cup transfer module including one or more analysis cup transfer components. The analysis cup transfer component completes the operation of transferring the coagulation test to the magnetic coagulation analysis channel of the magnetic coagulation analysis module by a transfer operation of the analysis cup.

In a preferred implementation, the optical coagulation analysis channel includes at least a light source component and a light reception component. The light reception component collects the optical signals of the transmitted light or the scattered light of the sample or the mixture of the sample and the reagent irradiated by the light source component to complete the coagulation test of the sample.

In a preferred implementation, the magnetic coagulation analysis channel includes a magnetic drive component and a particle displacement sensing component. The magnetic drive component drives the magnetically drivable particle to displace. The particle displacement sensing component detects a movement state of the particle and complete the coagulation test of the sample.

In a preferred implementation, the mixture of the sample and the reagent is a mixture of the sample and coagulation test reagent or a mixture of sample and a buffer solution. Preferably, the buffer solution is normal saline.

BRIEF DESCRIPTION OF THE DRAWINGS

In FIG. 2, 1 is analysis cup transfer module, 2 is incubation module, 3 is placing module of analysis cup without particle, 4 is discarded cup component, 5 is common module of optical coagulation analysis module and sample interference analysis module, 6 is placing module of analysis cup with magnetically drivable particle, 7 is magnetic coagulation analysis module, 8 is liquid transfer module, 9 is reagent placing module, 10 is sample tube, and 11 is sample tube placing module.

In FIG. 3, 1 is analysis cup transfer module, 3 is placing module of analysis cup without particle, 4 is discarded cup component, 15 is common module of optical coagulation analysis module and incubation module, 6 is placing module of analysis cup with magnetically drivable particle, 7 is magnetic coagulation analysis module, 8 is liquid transfer module, 9 is reagent placing module, 10 is sample tube, 12 is light source component of sample interference analysis module, 13 is light reception component of sample interference analysis module, and 14 is sample tube placing tray.

In FIG. 4, 1 is analysis cup transfer module, 2 is incubation module, 3 is placing module of analysis cup without particle, 4 is discarded cup component, 5 is common module of optical coagulation analysis module and sample interference analysis module, 7 is magnetic coagulation analysis module, 8 is liquid transfer module, 9 is reagent placing module, 10 is sample tube, 11 is sample tube placing module, and 16 is magnetically drivable particle automatic loading module.

In FIG. 5, 12 is light source component of sample interference analysis module, 13 is light reception component of sample interference analysis module, and 17 is to-be-analyzed sample.

In FIG. 6, 18 is light source component of optical coagulation analysis module, 19 is light reception component of optical coagulation analysis module, 20 is optical filter, 21 is analysis cup without particle, 22 is operational amplifier pre-processing circuit, 23 is AD acquisition circuit, 24 is microprocessor.

In FIG. 7, 25 and 26 are magnetic drive components, 27 is emission end of magnetic particle displacement sensing component, 28 is reception end of magnetic particle displacement sensing component, 29 is analysis cup with magnetically drivable particle, and 30 is magnetically drivable particle.

DETAILED DESCRIPTION

In order to make the objectives, technical solutions, and advantages of the present invention more clear, the present invention will be described herein in detail hereinafter with reference to the drawings and embodiments. It should be understood that the specific embodiments described hereinafter are merely intended to explain the present invention, rather than limit the present invention.

Embodiment 1

Figure 2:
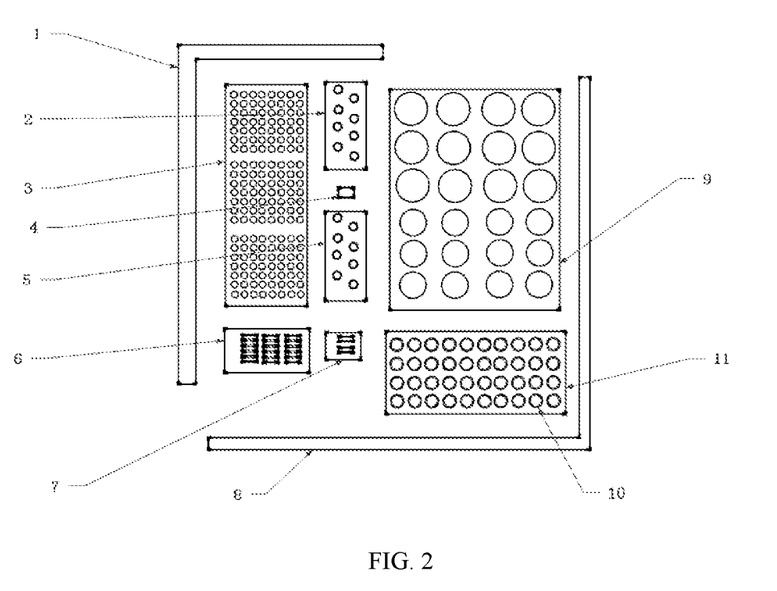
FIG. 2 is a top structural view of a coagulation analyzer according to embodiment 1 of the present invention.

One of the embodiments of the present invention is shown in FIG. 2, where 1 is analysis cup transfer module, 2 is incubation module, 3 is placing module of analysis cup without particle, 4 is discarded cup component, 5 is common module of optical coagulation analysis module and sample interference analysis module, 6 is placing module of analysis cup with magnetically drivable particle, 7 is magnetic coagulation analysis module, 8 is liquid transfer module, 9 is reagent placing module, 10 is sample tube, and 11 is sample tube placing module.

As shown in FIG. 2, the present invention provides a coagulation analyzer including a common module of optical coagulation analysis module and sample interference analysis module 5. The optical coagulation analysis module uses the analysis cup without particle for optical coagulation analysis. The sample interference analysis module is used to analyze the effect of sample interference on the optical coagulation analysis and determine the coagulation test affected by the sample interference. The coagulation analyzer further includes magnetic coagulation analysis module 7 which uses the analysis cup with magnetically drivable particle for a magnetic coagulation analysis. The coagulation analyzer further includes liquid transfer module 8 i.e. test transfer module for transferring the coagulation test affected by the sample interference to the magnetic coagulation analysis module.

The coagulation analyzer uses the sample interference analysis module to determine whether the interferent in the sample has effect on the coagulation test result of the optical coagulation analysis module. If the interferent in the sample has no effect on the coagulation test result, the optical coagulation analysis module is used to perform the coagulation analysis and report the test result. If the interferent in the sample has effect on the coagulation test result, the test transfer module is used to transfer the test to the magnetic coagulation analysis module to perform the coagulation analysis and report the test results.

In the embodiment, module 5 is the common module of the optical coagulation analysis module and the sample interference analysis module which share all module components. Module 5 has a thermostatic control, and the center temperature is preferably set at 37° C.

In the embodiment, incubation module 2 which only has an incubation function is separately provided. The analysis cup placing position area of incubation module 2 has a constant temperature incubation function, and the center temperature is preferably set at 37° C.

Sample tube 10 containing the sodium citrate anticoagulated plasma sample after centrifugation is stored in sample tube placing module 11.

Figure 9:
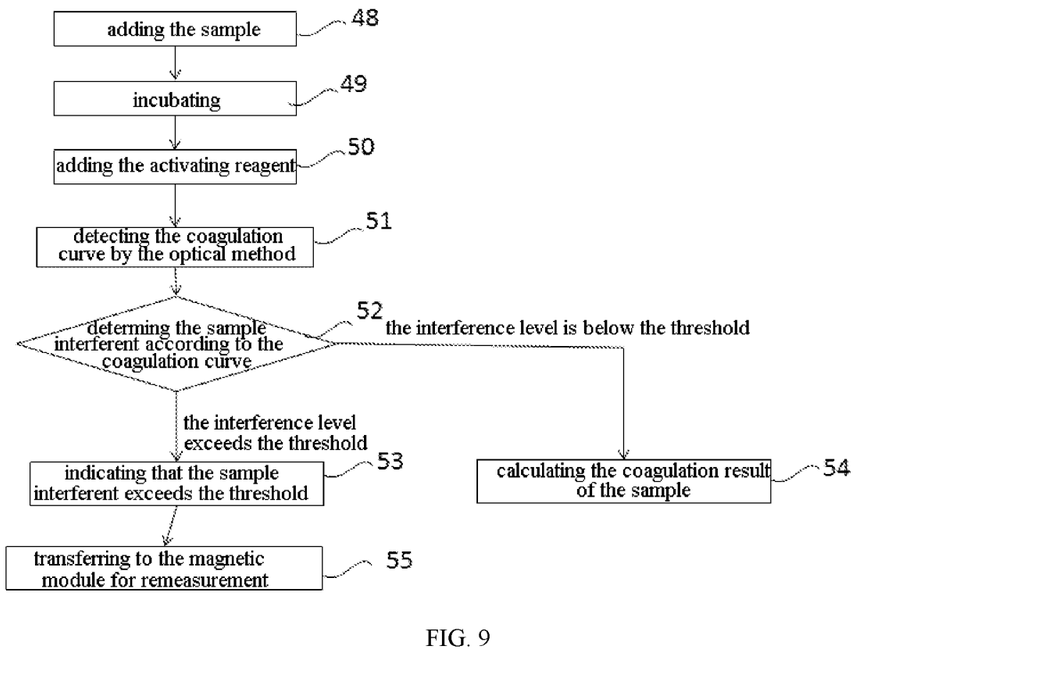
FIG. 9 is a test flow chart of sample interference determination during the coagulation test according to the present invention.

In the embodiment, the effects of interference on the coagulation test is determined during the coagulation test. FIG. 9 is a measurement implementation process taking prothrombin time (PT) as an example to explain how to determine the effects of interference during the coagulation test and decide whether the test needs to use the magnetic coagulation analysis module.

Analysis cup transfer module 1 transfers the analysis cups without particle in analysis cup placing module 3 to respective analysis cup placing position area on incubation module 2. As shown in FIG. 9, liquid transfer module 8 completes the step 48 of adding the sample to the analysis cup in the incubation module 2. After the incubation step 49, analysis cup transfer module 1 transfers the analysis cup to the common module 5 of optical coagulation analysis module and sample interference analysis module, liquid transfer module 8 completes the step 50 of adding the coagulation activating reagent. In the follow-up step 51, the optical signals of the mixture of the sample and the reagent are detected, the light beams emitted by the light source component of the common module 5 of optical coagulation analysis module and sample interference analysis module passes through the mixture of the sample and reagent in the analysis cup, and the light reception component of module 5 receives the optical signals.

In step 52, the effects of the sample interferent is determined according to the optical signals of the mixture of sample and reagent. Preferably, the specific determination algorithm includes selecting more than 100 samples having no effect on the coagulation test result (including samples without optical interference and samples with a low content of the optical interferent which is insufficient to affect the coagulation test result); measuring the transmitted light intensity of the mixture of sample and reagent in normal sate without effects; calculating the absorbance values; counting the distribution of the absorbance values and setting the threshold. When the sample is tested, after the mixture of sample and reagent in the analysis cup to be recognized is irradiated by the light source component, the light reception component acquires the intensity signal of the transmitted light and calculates the absorbance value. If the absorbance value exceeds the preset threshold, it is determined that there is a risk that the sample interference affects the coagulation test. In the embodiment, preferably, the absorbance value within 3 seconds after the sample and reagent are mixed is selected, so as to avoid the effects of the blood clotting response.

In the embodiment, liquid transfer module 8 is the test transfer module. For a coagulation test being determined to have sample interference, as shown in FIG. 9, step 53 is performed to indicate that the sample interferent goes beyond the threshold. Analysis cup transfer module 1 discards the analysis cup of step 52 to discarded cup component 4. As shown in step 55 of FIG. 9, the magnetic bead method channel is started for remeasurement. Liquid transfer module 8 refills the sample and the reagent in the analysis cup with magnetically drivable particle on magnetic coagulation analysis module 7, thereby transferring the coagulation test to magnetic coagulation analysis module 7 to complete the coagulation analysis, and reporting the test results. For the coagulation test which is not transferred to magnetic coagulation analysis module 7, the sample coagulation test result of the sample is calculated according to step 54 shown in FIG. 9. Subsequently, optical coagulation analysis module 5 completes the coagulation measurement in the analysis cup without particle of step 52 and reports the test result.

Figure 11:
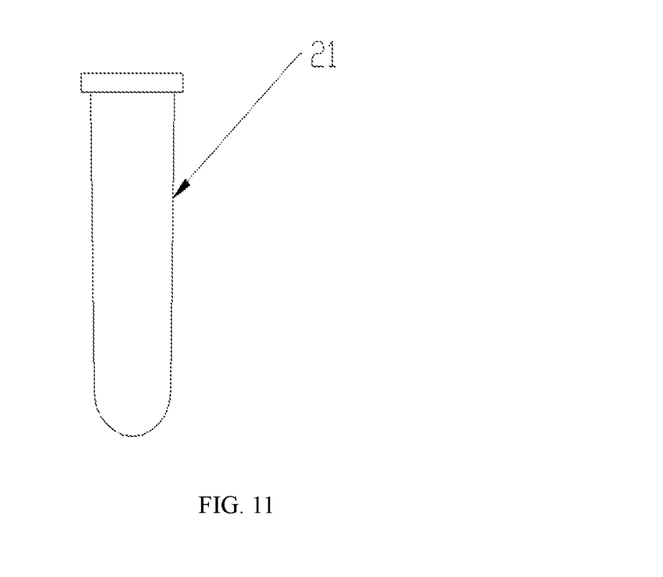
FIG. 11 is a structural schematic view of the analysis cup without particle of the present invention.
Figure 12:
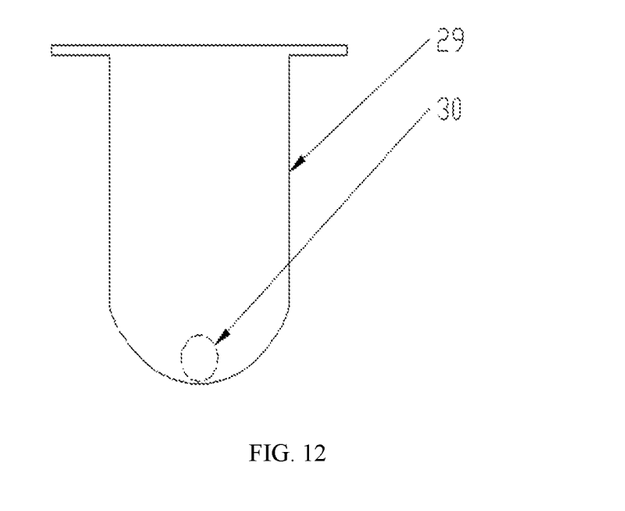
FIG. 12 is a structural schematic view of the analysis cup with the magnetically drivable particle of the present invention.

As shown in FIGS. 11 and 12, analysis cup transfer module 1 not only can be used to automatically transfer the analysis cup 21 without particle, and manually transfer the analysis cup with magnetically drivable particle from module 6 to module 7, but also can be used to automatically transfer the analysis cup 21 without particle and the analysis cup 29 with magnetically drivable particle.

Figure 6:
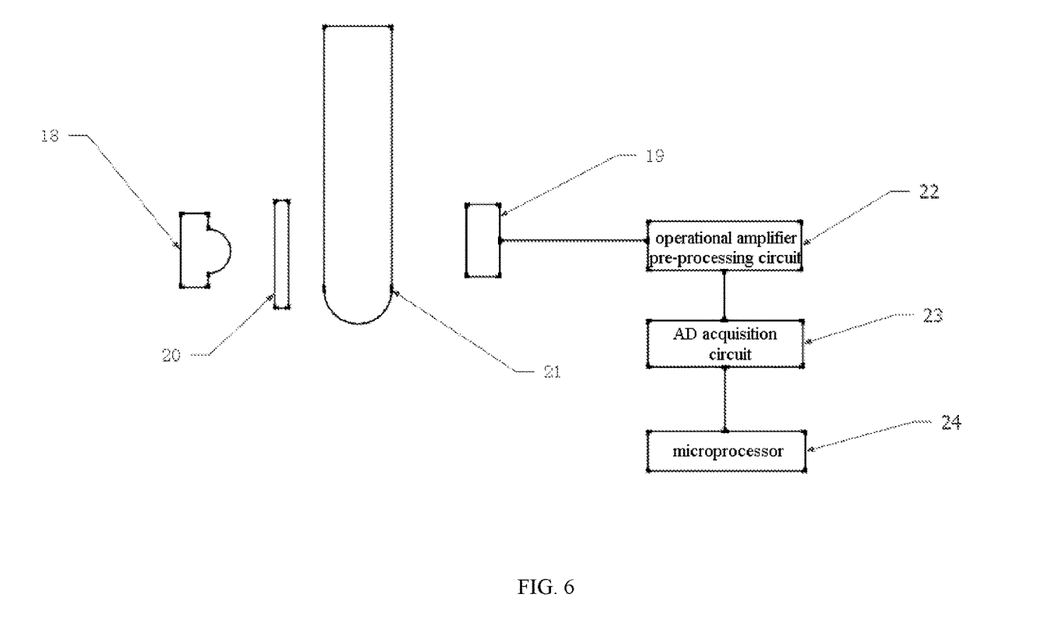
FIG. 6 is a structural schematic view of a measurement channel of an optical coagulation analysis module of the present invention.

FIG. 6 shows a measurement channel of the common module 5 of optical coagulation analysis module and sample interference analysis module. 18 is light source component of the optical coagulation analysis module, 19 is light reception component of the optical coagulation analysis module, 20 is optical filter, 21 is analysis cup without particle, 22 is operational amplifier pre-processing circuit, 23 is AD acquisition circuit, 24 is microprocessor. The common module 5 of optical coagulation analysis module and sample interference analysis module may include a plurality of measurement channels. The plurality of measurement channels may share components such as light source component 18, AD acquisition circuit 23, and microprocessor 24 etc. The light beam emitted by light source component 18 passes through the optical filter 20 of the measurement channel and irradiates the to-be-analyzed liquid in analysis cup 21. The transmitted light beam is received by the light reception component 19. The response signal of light reception component 19 is amplified and filtered by the operational amplifier pre-processing circuit 22, then subjected to a digital-to-analog conversion by the AD acquisition circuit 23, and finally input to the microprocessor 24 for digital signal processing. Preferably, light source component 18 is an LED, and light reception component 19 is a photodiode. The optical filter 20 may be placed at the end of light source component 18 or at the end of light reception component 19.

Figure 7:
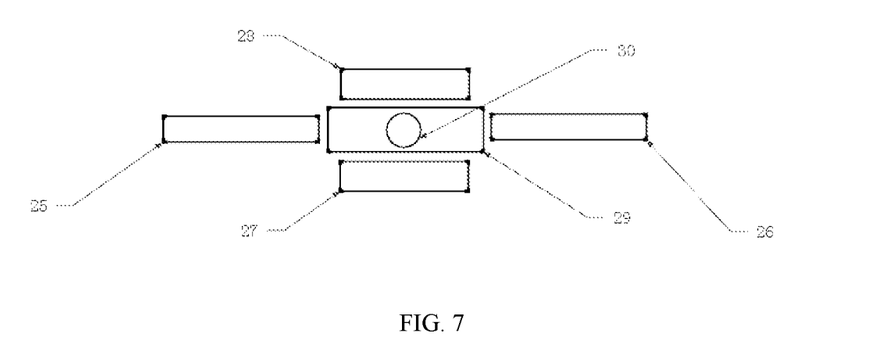
FIG. 7 is a structural schematic view of a measurement channel of a magnetic coagulation analysis module of the present invention.

FIG. 7 shows a measurement channel of the magnetic coagulation analysis module 7, which may include a plurality of measurement channels. 25 and 26 are magnetic drive components. Preferably, the magnetic drive component is magnetic particle displacement sensing component. 27 is emission end of the magnetic particle displacement sensing component, 28 is reception end of the magnetic particle displacement sensing component, 29 is analysis cup with magnetically drivable particle, and 30 is magnetically drivable particle. The magnetically drivable particle 30 may be displaced under the drive of the magnetic drive components 25 and 26. The magnetic signal emitted from emission end 27 is modulated by the displacement of the particle. The magnetic signal with particle movement information is received by reception end 28, and the particle movement state analysis is completed by the backend software and hardware. The particle movement state reflects the coagulation process, thus the clot time can be obtained through analysis.

Embodiment 2

Figure 3:
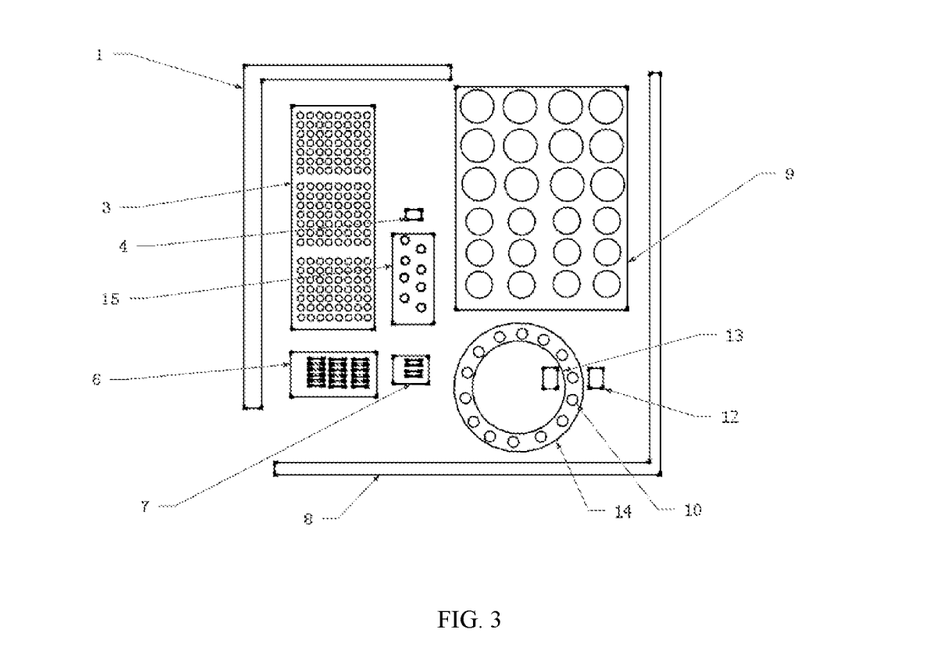
FIG. 3 is a top structural view of a coagulation analyzer according to embodiment 2 of the present invention.

Another embodiment of the present invention is shown in FIG. 3, where 1 is analysis cup transfer module, 3 is placing module analysis cup without particle, 4 is discarded cup component, 15 is common module of optical coagulation analysis module and incubation module, 6 is placing module of analysis cup with magnetically drivable particle, 7 is magnetic coagulation analysis module, 8 is liquid transfer module, 9 is reagent placing module, 10 is sample tube, 12 is light source component of the sample interference analysis module, 13 is light reception component of the sample interference analysis module, and 14 is sample tube placing tray.

Figure 5:
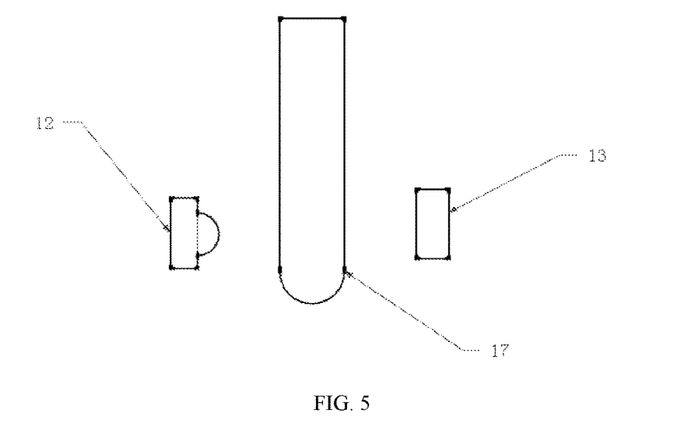
FIG. 5 is a structural schematic view of a measurement channel of a sample interference analysis module of the present invention.

FIG. 5 shows an example of measurement channel of the sample interference analysis module. The sample interference analysis module includes a plurality of measurement channels. 12 is light source component of the sample interference analysis module, 13 is light reception component of the sample interference analysis module, and 17 is sample to be analyzed.

According to the embodiment shown in FIG. 3, the sample tube is placed in sample tube placing tray 14 that is rotatable. Light source component 12 of the sample interference analysis module is assembled outside the sample tube placing tray, and the light reception component 13 of the sample interference analysis module is assembled inside sample tube placing tray. The light beam emitted from light source module 12 passes through the sample tube 10 on the sample tube placing tray, and the optical signal is received by light reception module 13.

More than 100 samples having no effect on the coagulation test result (including samples without optical interference and samples with a low content of the optical interferent which is insufficient to affect the coagulation test result) are selected to measure the transmitted light intensity in the normal sate without effects, then the absorbance value is calculated, the distribution of the absorbance value is counted, and the threshold is set. When the sample is tested, after the to-be-recognized sample tube is irradiated by the light source component, the light reception component acquires the transmitted light intensity signal and calculates the absorbance value. If the absorbance value exceeds the preset threshold, it is determined that there is a risk that the sample interference affects the coagulation test.

In the embodiment, liquid transfer module 8 is the test transfer module. For the coagulation test being determined to have sample interference, liquid transfer module 8 transfers the coagulation test to magnetic coagulation analysis module 7 to complete the coagulation analysis and report the test result. The coagulation test that is not transferred to the magnetic coagulation analysis module 7 is completed in the common module 15 of optical coagulation analysis module and incubation module and the test results are reported. In the embodiment, the optical coagulation analysis module and the incubation module completely share the same module, and no incubation module that only has incubation function is separately provided.

The analysis cup transfer module 1 not only can be used to automatically transfer the analysis cup 21 without particle, and manually transfer the analysis cup with magnetically drivable particle from module 6 to module 7, but also can be used to automatically transfer the analysis cup 21 without particle and the analysis cup 29 with magnetically drivable particle.

Figure 10:
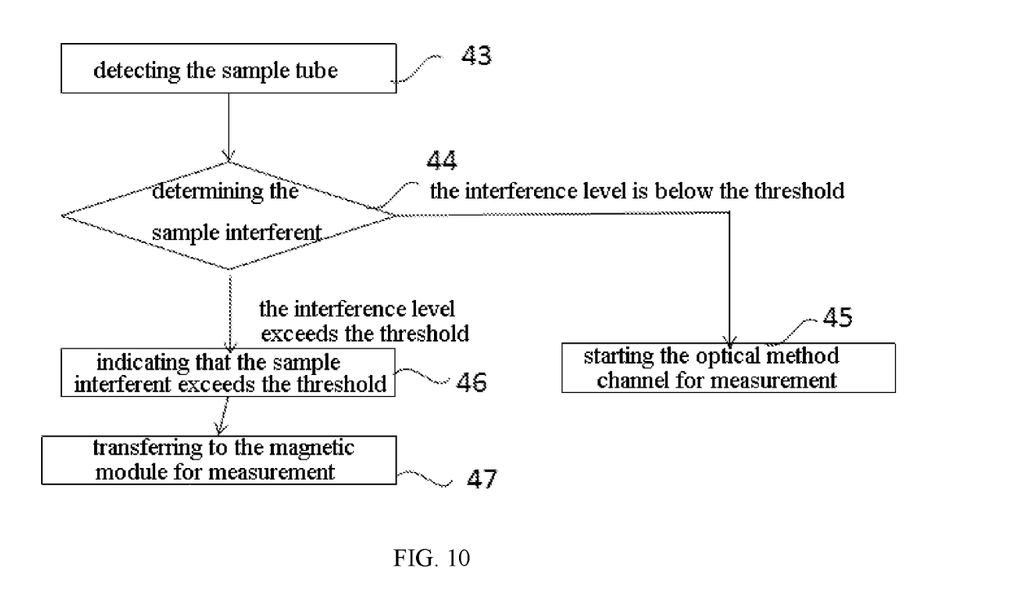
FIG. 10 shows a test flow of interferent detection and determination in the sample tube according to the present invention.

FIG. 10 is a determination flowchart showing the scanning method of sample tubes. Step 43 is the detection of the sample tubes, step 44 is the determination of the effects of sample interferent on coagulation test results. If the interference level is less than the threshold, step 45 is started to complete coagulation analysis by using the optical coagulation analysis module. If the interference level is more than the threshold, go to step 46 to indicate that the sample interferent goes beyond the threshold, then step 47 is performed to complete the coagulation analysis by the magnetic coagulation analysis module.

Embodiment 3

Figure 4:
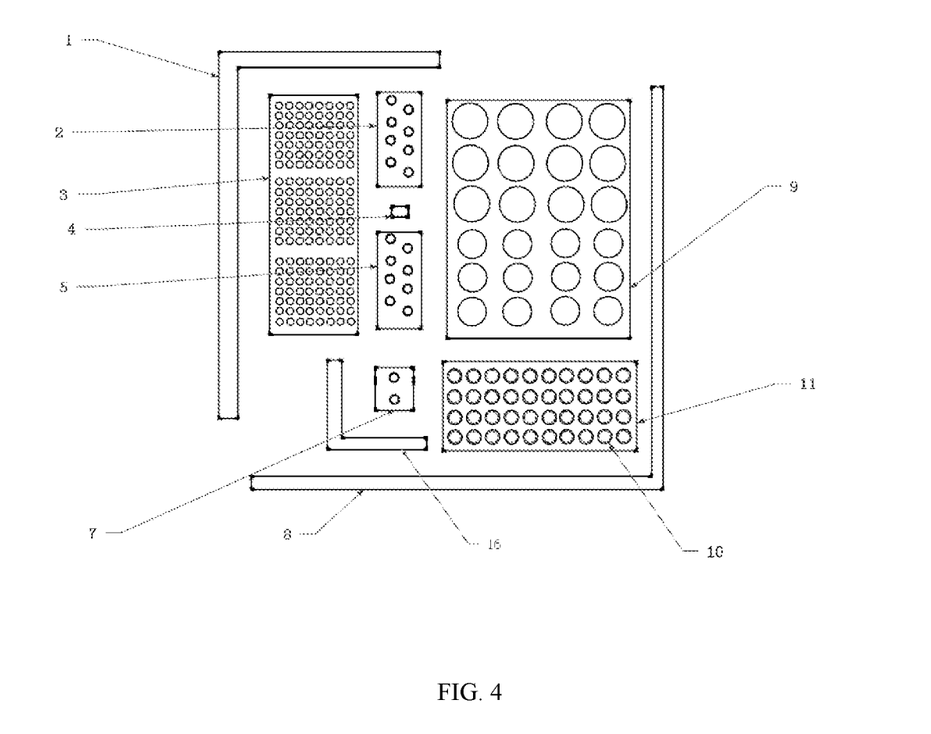
FIG. 4 is a top structural view of a coagulation analyzer according to embodiment 3 of the present invention.

Another embodiment of the present invention is shown in FIG. 4, where 1 is analysis cup transfer module, 2 is incubation module, 3 is placing module of analysis cup without particle, 4 is discarded cup component, 5 is common module of optical coagulation analysis module and sample interference analysis module, 7 is magnetic coagulation analysis module, 8 is liquid transfer module, 9 is reagent placing module, 10 is sample tube, 11 is sample tube placing module and 16 is magnetically drivable particle automatic loading module.

In the embodiment, module 5 is the common module of optical coagulation analysis module and sample interference analysis module which share all module components. Module 5 has a thermostatic control, and the center temperature is preferably set at 37° C.

Figure 8:
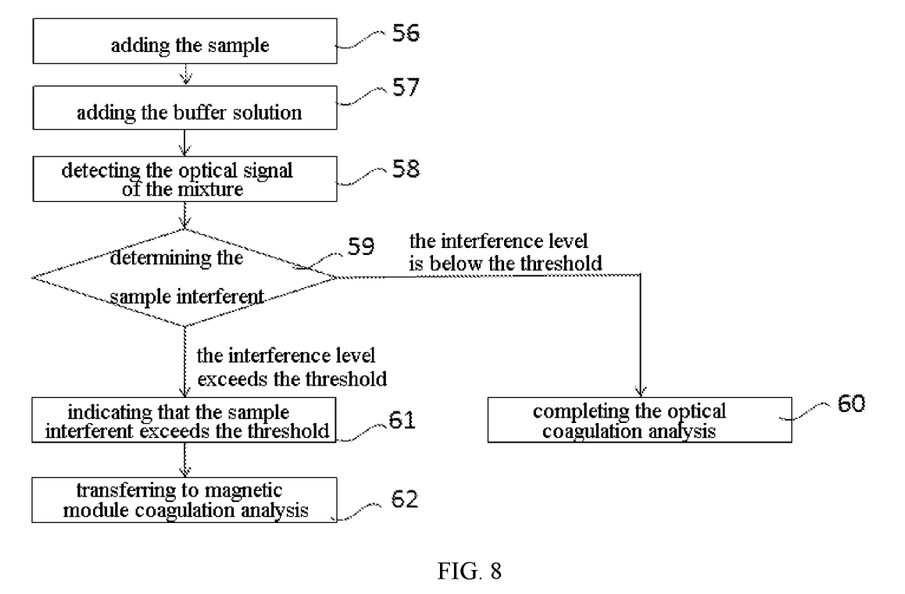
FIG. 8 is a flow chart of sample interference determination and measurement of a mixture of sample and buffer solution according to the present invention.

Analysis cup transfer module 1 transfers the analysis cups without particle in analysis cup placing module 3 to respective analysis cup placing position at the module 5. As shown in FIG. 8, the step 56 of adding the sample and the step 57 of adding the buffer solution to the analysis cup in module 5 are completed by liquid transfer module 8. In the follow-up step 58, the optical signal of the mixed solution is detected, the light beam emitted by the light source module of module 5 passes through the mixture of sample and buffer solution in the analysis cup, and the optical signals are received by the light reception module of module 5. Preferably, the buffer solution is normal saline.

In step 59, the effects of the sample interferent are determined according to the optical signals of the mixture of sample and buffer solution. Preferably, the specific determination algorithm includes selecting more than 100 samples having no effect on the coagulation test result (including samples without optical interference and samples with a low content of the optical interferent which is insufficient to affect the coagulation test result); measuring the transmitted light intensity of the mixture of sample and buffer solution in normal state without effect; calculating the absorbance value, counting the distribution of the absorbance value, and setting the threshold. When the sample is tested, after the mixture of sample and buffer solution in the analysis cup to be recognized is irradiated by the light source component, the light reception component acquires the transmitted light intensity signal and calculates the absorbance value. If the absorbance value exceeds the preset threshold, it is determined that there is a risk that the sample interference affects the coagulation test.

In the embodiment, analysis cup transfer module 1 is the test transfer module. For the coagulation test being determined to have the sample interference, analysis cup transfer module 1 transfers the analysis cup without particle of the coagulation test to the magnetic coagulation analysis module 7. Magnetically drivable particle automatic loading module 16 adds the magnetically drivable particle to the analysis cup as shown in step 62 of FIG. 8. The coagulation analysis is completed by the magnetic coagulation analysis module 7 and the test results are reported. For the coagulation test that is not transferred to magnetic coagulation analysis module 7, as shown in step 60 of FIG. 8, the coagulation measurement is completed in the optical coagulation analysis module 5 and the test results are reported.

In the embodiment, incubation module 2 that only has an incubation function is separately provided. The analysis cup placing area of incubation module 2 has a constant temperature incubation function, and the center temperature is preferably set at 37° C.

The above-mentioned embodiments are merely preferred embodiments of the present invention and are not intended to limit the present invention. Any modification, equivalent, combination, and improvement derived within the spirit and principle of the present invention shall fall within the scope of the present invention.

The invention claimed is:

1. A coagulation analyzer, comprising:
   a sample interference analysis module, which is configured to test a sample and determine whether an interferent in the sample has effect on an optical coagulation test result by comparing an absorbance value of the sample with a preset threshold, wherein the preset threshold is determined by a distribution of a plurality of absorbance values of a plurality of samples having no effect on the optical coagulation test result;
   an optical coagulation analysis module, which is configured for the optical coagulation test of the sample containing in an analysis cup without particle, wherein the interferent in the sample has already been determined by the sample interference analysis module to have no effect on the optical coagulation test result, and the optical coagulation test of the sample is achieved using a method selected from a group consisting of coagulation method, colorimetry, immunonephelometry, and a combination thereof; and
   a magnetic coagulation analysis module, which is configured for a magnetic coagulation test of the sample containing in an analysis cup with a magnetically drivable spherical particle using a coagulation method, wherein the interferent in the sample has already been determined by the sample interference analysis module to have effect on the optical coagulation test result using a coagulation method, and the magnetic coagulation analysis module comprises a magnetic drive component and a particle displacement sensing component, wherein the magnetic drive component is configured to drive the magnetically drivable spherical particle to displace, and the particle displacement sensing component comprises a magnetic signal emission portion which is configured for emitting a magnetic signal to the displacing magnetically drivable spherical particle, and a magnetic signal reception portion which is configured for receiving the magnetic signal with a displacement information of the displacing magnetically drivable spherical particle so as to detect a movement state of the magnetically drivable spherical particle, thereby calculating a blood coagulation time and completing the magnetic coagulation test of the sample, and wherein the magnetic coagulation analysis module and the optical coagulation analysis module are two different analysis modules; and wherein the coagulation analyzer is configured so that, when the sample interference analysis module determines that the interferent in the sample has no effect on the optical coagulation test result, the optical coagulation analysis module is configured to carry out the optical coagulation test in an analysis cup without particle, and when the sample interference analysis module determines that the interferent in the sample has effect on the optical coagulation test result using the coagulation method, the sample is automatically transferred to the magnetic coagulation analysis module to carry out the magnetic coagulation test in the analysis cup with magnetically drivable spherical particle.

2. The coagulation analyzer of claim 1, wherein
the sample interference analysis module comprises a first light source component, a first light reception component, and a sample interference data processing unit; wherein
the first light source component is configured to irradiate the sample;
the first light reception component is configured to collect a first optical signal of a transmitted light or a scattered light through the sample; and
the sample interference data processing unit is configured to determine whether the interferent in the sample has effect on the optical coagulation test by comparing the absorbance value of the sample with the preset threshold.

3. The coagulation analyzer of claim 2, wherein
the optical coagulation analysis module comprises a second light source component and a second light reception component; wherein
the second light source component is configured to irradiate the sample;
the second light reception component is configured to collect a second optical signal of a transmitted light or a scattered light through the sample to complete the optical coagulation test of the sample.

4. The coagulation analyzer according to claim 3, wherein
the first light source component and the second light source component are the same component.

5. The coagulation analyzer of claim 3, wherein
the first light reception component and the second light reception component are the same component.

6. The coagulation analyzer of claim 1, wherein
the magnetically drivable spherical particle has already been pre-loaded into the analysis cup, or is configured to be automatically loaded into the analysis cup.

7. The coagulation analyzer of claim 1, wherein
the sample is configured to be directly transferred in a liquid form into the analysis cup at the magnetic coagulation analysis module for the magnetic coagulation test of the sample.

8. The coagulation analyzer of claim 1, wherein
the sample is configured to be held in the analysis cup and the analysis cup with the sample is automatically transferred to the magnetic coagulation analysis module for the magnetic coagulation test of the sample.

9. The coagulation analyzer of claim 1, wherein
the analysis cup without particle and the analysis cup with magnetically drivable spherical particle have different geometrical structural characteristics.

10. The coagulation analyzer of claim 2, wherein
the sample interference data processing unit is configured so that, when the absorbance value exceeds beyond the preset threshold, the sample interference data processing unit determines the interferent in the sample has effect on the optical coagulation test, and when the absorbance value does not exceed beyond the preset threshold, the sample interference data processing unit determines the interferent in the sample has no effect on the optical coagulation test.

11. The coagulation analyzer of claim 1, wherein the optical coagulation analysis module and the sample interference analysis module are the same analysis module, wherein,
when the sample interference analysis module determines that the interferent in the sample has no effect on the optical coagulation test result, the sample would not be transferred and is held at the sample interference analysis module for the optical coagulation test, and when the sample interference analysis module determines that the interferent in the sample has effect on the optical coagulation test result, the sample is automatically transferred to the magnetic coagulation analysis module for the magnetic coagulation test.

12. The coagulation analyzer of claim 1, wherein the optical coagulation analysis module and the sample interference analysis module are two different analysis modules, wherein,
when the sample interference analysis module determines that the interferent in the sample has no effect on the optical coagulation test result, the sample is transferred to the optical coagulation analysis module for the optical coagulation test, and when the sample interference analysis module determines that the interferent in the sample has effect on the optical coagulation test result, the sample is automatically transferred to the magnetic coagulation analysis module for the magnetic coagulation test.

* * * * *